(12) United States Patent
Bedingfield

(10) Patent No.: US 7,911,353 B2
(45) Date of Patent: Mar. 22, 2011

(54) VERIFYING SPEAKER OPERATION DURING ALARM GENERATION

(75) Inventor: John A. Bedingfield, Largo, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 330 days.

(21) Appl. No.: 12/131,751

(22) Filed: Jun. 2, 2008

(65) Prior Publication Data

US 2009/0295591 A1  Dec. 3, 2009

(51) Int. Cl.
*G08B 21/00* (2006.01)
(52) U.S. Cl. ............... 340/660; 340/657; 340/664
(58) Field of Classification Search .......... 340/660–664, 340/657; 381/59, 86; 324/503
See application file for complete search history.

(56) References Cited

U.S. PATENT DOCUMENTS

| | | | |
|---|---|---|---|
| 4,037,222 A * | 7/1977 | Solomon | 181/139 |
| 4,881,058 A * | 11/1989 | Berry, III | 340/326 |
| 5,736,927 A | 4/1998 | Stebbins et al. | |
| 6,094,134 A | 7/2000 | Cohen | |
| 6,462,652 B1 | 10/2002 | McCuen et al. | |
| 6,545,533 B2 | 4/2003 | Karki et al. | |
| 7,106,193 B2 | 9/2006 | Kovach | |
| 2003/0073408 A1 | 4/2003 | Harrell et al. | |
| 2007/0146127 A1 | 6/2007 | Stilp et al. | |

FOREIGN PATENT DOCUMENTS

| | | |
|---|---|---|
| EP | 0715425 | 6/1996 |
| GB | 2390908 | 1/2004 |

OTHER PUBLICATIONS

International Search Report and Written Opinion for International Application No. PCT/US2009/045784 mailed on Nov. 12, 2009.

* cited by examiner

*Primary Examiner* — Anh V La
(74) *Attorney, Agent, or Firm* — K&L Gates LLP

(57) ABSTRACT

The patent discloses a method of verifying that a dialysis machine audio alarm has been sounded. The method senses a waveform of electric power, such as a waveform of the current or voltage that drives a speaker. When the speaker produces sound, power consumption changes the waveform in a manner that is detectable by electrical and electronic sensors. The amplitude envelope and frequency or period of the waveform is specific to the electrical and mechanical characteristics of the speaker. The waveform may be detected by a current-sensing resistor in series with the speaker power source, by a non-contact current transformer or hall-effect sensor, or may be sampled by an ADC. A computer program then compares this resulting signal to an expected signal or waveform and verify the speaker is working. If the speaker is not working, the machine sends a visual alarm or places itself in a safe state.

24 Claims, 5 Drawing Sheets

PWM Voltage Waveform

VERIFYING SPEAKER OPERATION DURING ALARM GENERATION

BACKGROUND

The present patent relates to verification that an audio alarm has been sounded by a speaker upon activation of the alarm from a controller or other device. The verification particularly relates to patients using medical machines, such as dialysis machines, and even more particularly extracorporeal blood machines, such as hemodialysis machines, apheresis machines, and heart-lung operation machines.

Modern medical machines perform a variety of life-sustaining and life-preserving tasks, from peritoneal dialysis and hemodialyis, to plasmapheresis, and even performing blood circulation and oxygenation that allows surgeons to perform medical procedures during a heart-bypass operation. Of course, machines are not perfect and conditions can arise during their use that threatens the completion or the quality of the procedure. For example, if a peristaltic pump is used to convey blood within tubing, the pump head could break, the motor could stall, and the tubing could develop leaks. Sensors on the instrument would detect these conditions in at least one way, such as a loss of blood pressure or a drop in motor current.

If one of these failures occurred, for example, during a coronary artery bypass procedure, an alert operator on the medical team would immediately detect the condition and would take action to substitute a back-up machine or otherwise correct the situation. Other procedures, however, may have only a single operator, such as a caregiver, or may have only the patient present while the procedure is performed. An example is plasmapheresis. Plasmapheresis typically takes place at a medical center, with a head nurse or other professional to supervise one or more patients undergoing the procedure. If a machine failure occurs, or an unsafe condition develops, the plasmapheresis machine may flash a warning light or a warning on a video screen, or more likely, sound an audio alarm, such as a buzzer. The audio alarm alerts the patient or a nurse or other caregiver, or both, that attention is needed. If for any reason the audio alarm does not sound, the patient or nurse may notice the visual alarm or alert and is then motivated to correct the situation.

The audio alarm may not sound if there is an alarm fault, such as a connectivity fault, in the chain between the machine fault or failure and the audio speaker that is intended to sound an alarm or alert as a result of the machine fault or failure, or other condition for which an alarm is desired. For example, an electrical wire may become disconnected from a speaker connection, or the wire may break, thus preventing an audio signal from reaching the speaker. Other electrical or physical problems could also result in a failure of the speaker to emit audible sound, such as failure of a relay within the control system, disconnection of power to an audio amplifier, or disconnection of a ground from the circuit.

If an audio alarm fails to sound through the speaker, as noted above, corrective action is needed but personnel may not be alerted to the need. There are several ways to detect the failure of the sound. For example, the machine of which the speaker is a part may be equipped with a local microphone for detection of sound from the speaker. If the machine control system attempts to sound an audio alarm, but the alarm is not detected by the microphone, the failure to detect is interpreted as a speaker or other system failure and corrective action can be taken. Examples are depicted in U.S. Pat. Nos. 5,736,927 and 6,094,134. However, this method requires a separate microphone near the speaker, an amplifier and tuner for the microphone, as well as tuning of the microphone, and additional programming to perform the analysis and then to follow up. In addition, this system would be subject to interference from nearby noise, possibly including interfering noise that would mask the speaker output from detection by the microphone.

What is needed is a way to ensure that when a medical device or machine sounds an alert or an alarm, that the intended speaker has actually sounded the alert or alarm. If the alarm has not been sounded, the medical device or machine is then programmed to take additional steps, such as sending a visual alert or alarm, or placing the machine in a safe mode.

SUMMARY

One embodiment is a method for verifying operation of a speaker for a dialysis machine. The method includes steps of generating an audio alarm for the dialysis machine by sending electric power to a speaker, sensing a waveform of the electric power, and verifying the waveform is consistent with power consumption by the speaker. For instance, this may be accomplished by comparing the waveform to a waveform from a known good speaker.

Another embodiment is a method for verifying speaker operation. The method includes steps of generating an audio alarm in a medical therapy machine by sending electric power to a speaker, sensing a waveform of the electric power, and verifying the waveform is consistent with power consumption by the speaker of the medical therapy machine by comparing an amplitude or a period of the waveform to a desired amplitude or period.

Another embodiment is a method of verifying speaker operation. The method includes steps of generating an audio alarm by sending electric power to a speaker for a medical therapy machine, sensing a current or a voltage of the electric power, and verifying with a computer program that the current or the voltage is consistent with power consumption by a known good speaker by comparing an amplitude portion or a period portion of the current or the voltage to a desired amplitude portion or desired period portion.

Additional features and advantages are described herein, and will be apparent from the following Detailed Description and the figures.

DETAILED DESCRIPTION

It is very important, and may be life-preserving, to note quickly when a medical instrument, such as a dialyzer or other extracorporeal instrument, sounds an alarm or sends a signal indicating that an operating parameter has been exceeded. There may be danger to the machine, or more importantly, a condition may exist that indicates a threat to the health or life of the patient using the machine.

Figure 1:
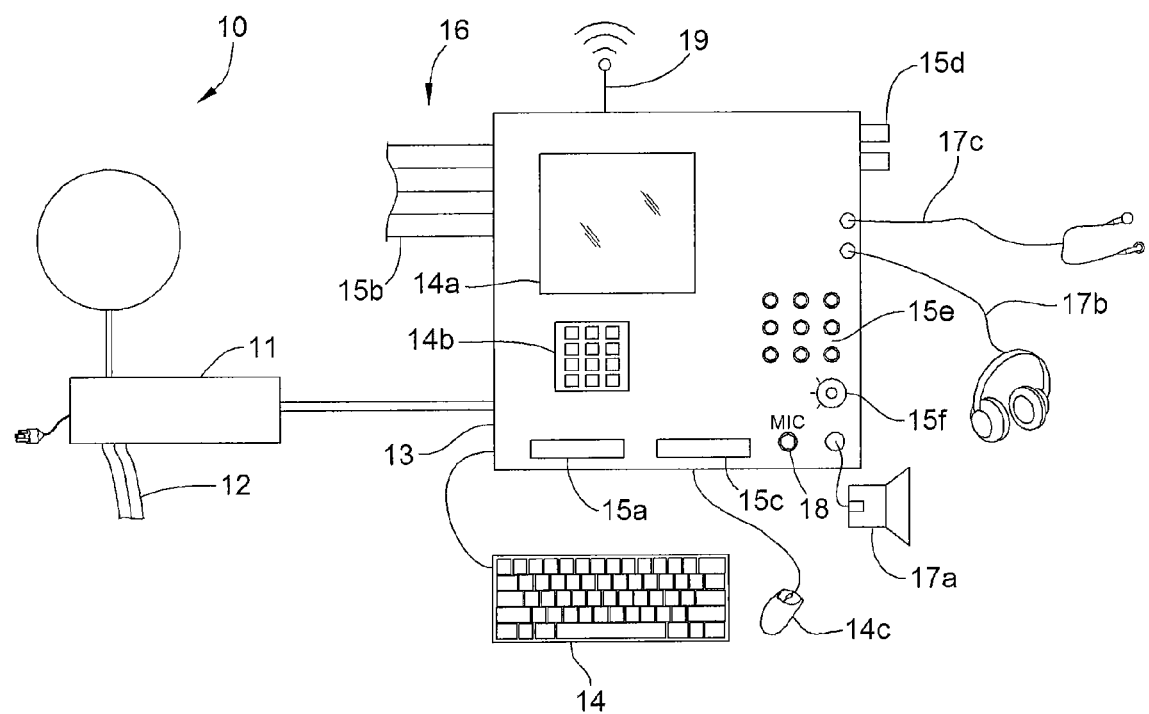
FIG. 1 depicts a dialyzer with a controller and an audio alarm.

An example of such a medical instrument is disclosed in FIG. 1. Medical instrument 10 may be a dialyzer or other medical instrument, including an operating portion 11 with fluid lines 12 for connection to a patient. An operating section 11 may perform dialysis or other therapeutic or diagnostic function for the patient under the supervision of a control section or computer 13. Control section or computer 13 has at least an input keypad 14, a video screen 14a, which may be a touch screen, an input number pad 14b, and a mouse 14c. The computer will also include input drive 15a, which may be suitable for a floppy drive or for a CD drive.

The computer is configured with a port for Internet access 15b, as well as additional inputs and outputs, including ports 16. The additional input ports may be any combination of serial ports, such as USB ports, or parallel ports. In some embodiments, the computer will be adapted to receive commands from a remote control unit, and will include an infrared receiver 15c for a hand-held remote. Inputs/outputs may include an optical input or output 15d and other digital or analog inputs. Control portion 15e includes a series of controls knobs or switches for operating the medical machine. There is also at least one lamp 15f, such as an LED, or flashing a visual alert. In order to sound an audio alarm, the instrument includes at least one speaker 17a, or alternately or in addition, headphones 17b or earbuds 17c. The instrument optionally includes a microphone connection 18, and an antenna 19 for receiving at least remote commands or information. The antenna may be used for wireless (WiFi) internet access or may be used for remote, but closer, commands.

Figure 2:
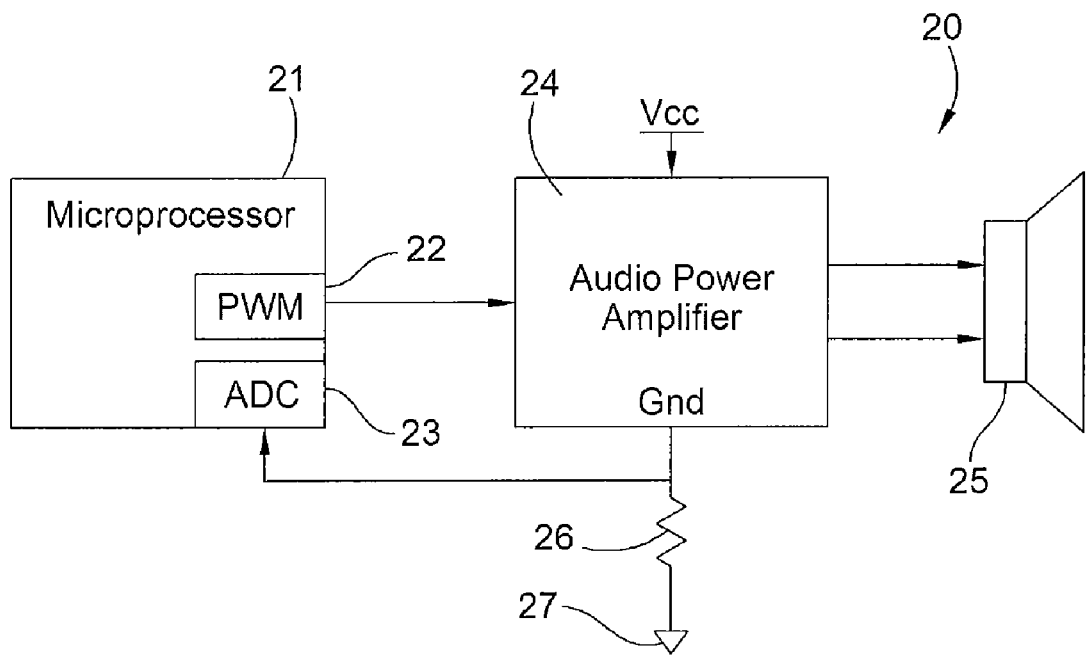
FIG. 2 is a schematic diagram of a circuit for verifying speaker operation during an alarm.

The medical instrument depicted in FIG. 1 is under the control of at least one microcontroller. The video screen 14a may also output a visual alarm. As noted, the instrument includes a speaker for sounding an audio alarm. One circuit for sounding the audio alarm or tone is depicted in FIG. 2. Alarm circuit 20 includes a microcontroller 21, which includes pulse-width modulation (PWM) module 22 and an analog-to-digital converter (ADC) 23. A voltage-signal output of the PWM module is sent to an audio power amplifier 24, which is connected to additional power Vcc. The amplifier amplifies the input PWM voltage signal and sends the amplified signal to speaker 25, when instructed to do so by the microcontroller. In order to detect current to the speaker, a current-sensing resistor 26 is placed between the speaker leads and ground 27. The current-sensing resistor is a very low value, such as a few milliohms. The signal produced by resistor 26 is then sent to ADC 23. The microcontroller 21 a memory or has access to a memory with a computer program or software algorithm for determining whether the waveform detected is a match with an expected waveform from the speaker.

Figure 3:
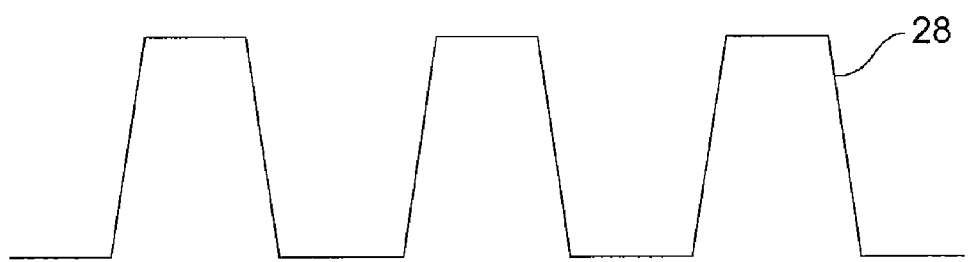
FIG. 3 depicts waveforms for electric power for detecting speaker operation.
Figure 3:
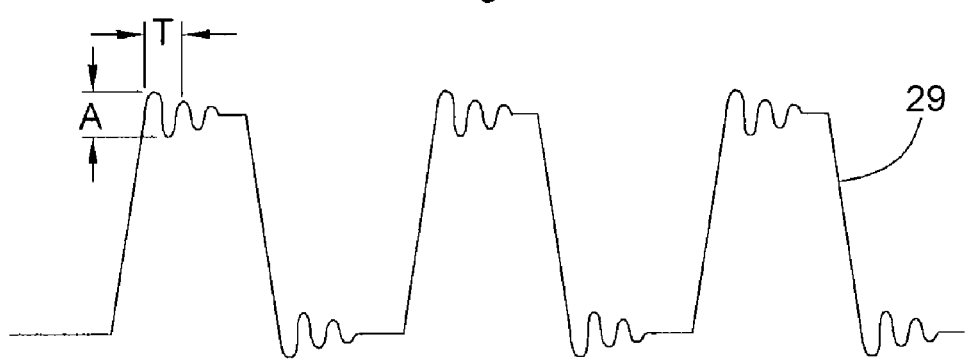

The upper portion of FIG. 3 depicts a square wave signal as it is sent to the amplifier, and the lower portion of FIG. 3 depicts the signal as it looks after it is amplified and sent to speaker 25. The speaker produces tones whose fundamental frequency equals that of the input square wave. The speaker produces a back electromotive force (EMF), as seen in the lower portion of FIG. 3, and each pulse is changed, acquiring a slight ringing or oscillation on the leading edge and trailing edge of the pulse. This ringing or oscillation is caused by the step-change nature of a square wave and its interaction with the speaker. Each step produces a ringing of amplitude A and period T, imposed atop the waveform. The ringing or oscillation in this example has about three cycles, each cycle with diminishing amplitude, before the waveform resumes a relatively constant value. As noted above, the waveforms of FIG. 3 depict current over a period of time. If, for example, the square wave is cycling at about 5 kHz, the period of each square wave is about 200 microseconds long, and the ringing in this instance lasts for about 25 microseconds per pulse, a frequency of about 40 kHz. Within reasonable limits, in the work done to date, the period T and the amplitude A are not affected by the frequency or duty cycle of the input square wave. The amplitude envelope and frequency or period of this waveform ringing are specific to the mechanical and electrical characteristics of the speaker, rather than of the input signal.

This system will detect several failure modes of the speaker. For example, if the speaker fails open, due to a broken wire in the speaker's voice coil, no current will flow and no current will be detected. No current will flow, no power will be delivered to the speaker, and no sound will be heard. As a result, no ringing or oscillation is possible because there is no current and no power. The system disclosed herein will detect the lack of current and will also detect the lack of ringing or oscillation. If the speaker fails shorted, excessive current will flow to the speaker, and this will also be detected. The disclosed system will note the lack of current or the high current as a failure and will respond with appropriate actions, such as using a visual alarm or placing the machine in a safe mode automatically. Furthermore, more subtle damage to the speaker, e.g., speaker cone damage, can also be detected since such damage will also cause a change in the ringing waveform.

Other circuits may also be used to detect a ringing or oscillation in the power for a positive indication that the speaker is operable and is working, i.e., converting electrical energy into acoustical energy. As noted, if there were an open in the circuit, no power would be consumed, and no current or voltage waveform would appear in certain parts of the circuit. If there is a disconnect between the PWM module and the amplifier, there is no signal to amplify and no current (or voltage) would appear on the outputs of the amplifier. If the connection between the power amplifier and the speaker is broken, no power will be applied to the speaker. If the speaker internal wiring (which may be modeled as a resistor and inductor in series) is severed or otherwise broken, the speaker will be inoperable and will not consume electricity. Of course, if there is a short circuit in any portion of the circuitry, the speaker may also be inoperable and will also not yield the desired or expected waveform. This method will also detect mechanical failures of the speaker itself, such as a damaged speaker cone or stuck speaker coil, and so forth, as well as the electrical failures discussed above. The circuit and technique described herein may be used to determine the condition of the speaker or alarm circuit of a dialyzer or other extracorporeal blood treatment machine.

Figure 4:
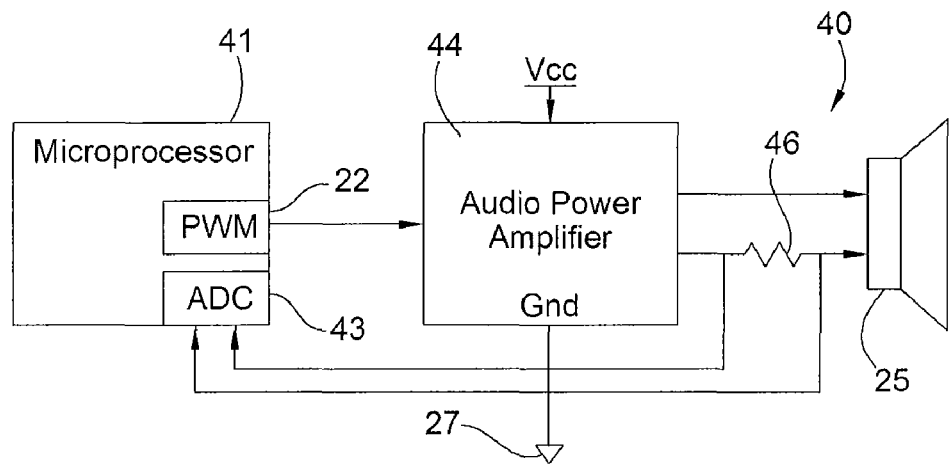
FIGS. 4-9 depict diagrams of alternate circuits for verifying speaker operation.
Figure 5:
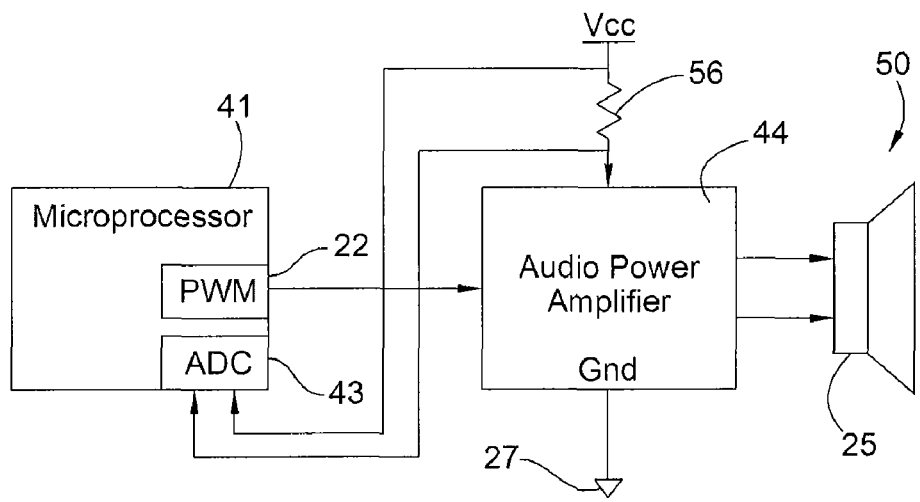

Other circuits, as shown in FIGS. 4-8 below, may also be used. FIG. 2 took advantage of the fact that electricity must complete a "current loop" or circuit in order for the circuit to function. FIGS. 4 and 5 use a different detection method, employing differential current or voltage detection and a differential ADC to detect the resultant waveform. In FIG. 4, waveform detection circuit 40 includes a microcontroller 41, a PWM module 22, and a differential ADC 43. The differential ADC accepts two inputs as shown from resistor 46, which is connected in series between the audio power amplifier 44 and the speaker 25. ADC 43 determines the differences between the inputs. This data is then used by a software program in microcontroller 41 to determine whether the waveform detected is indicative of a speaker that is working or of a speaker that is not working. The software program may be the same as the program in microcontroller 21 or may be different, tailored for differential inputs. In this example, the current-sensing resistor 46 is placed in series with one of the speaker leads. Since neither end of the resistor is referenced to ground, the differential ADC is needed. In the example of FIG. 5, detector circuit 50 includes a current sensing resistor 56 placed in series with the amplifier power source, Vcc. This differential circuit will function in a manner very similar to that of FIG. 4. Note that if the speaker is not operating, Vcc will not be called upon to supply power to the amplifier and the speaker, and the current or voltage sensed will be only quiescent current or voltage.

Figure 6:
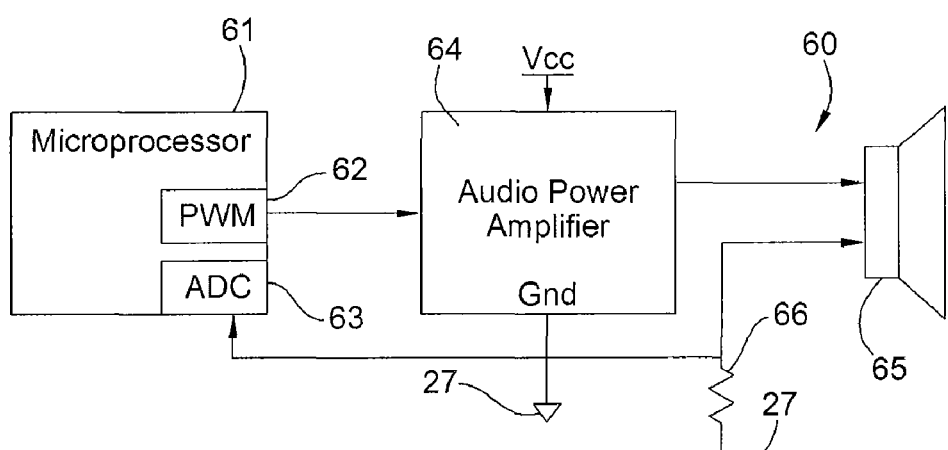
Figure 7:
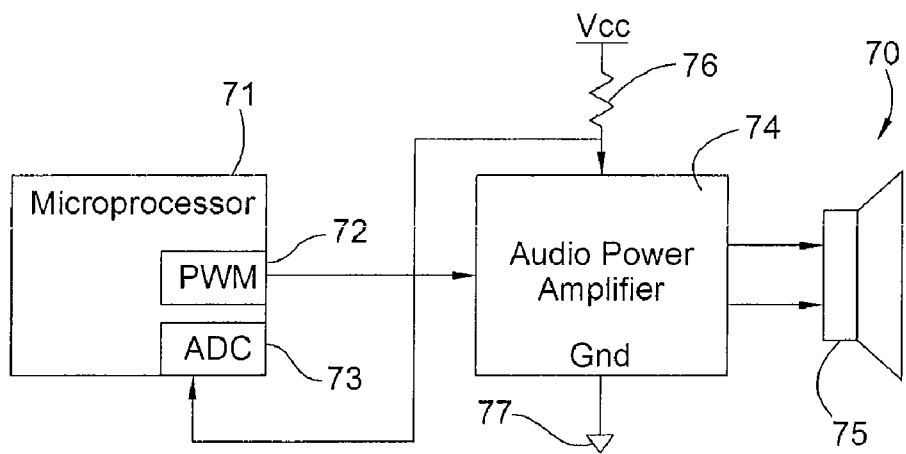

Other variations of an alarm circuit 60 may also be used, as depicted in FIG. 6, which uses a grounded speaker 65 and resistor 66, which is configured as a voltage input to ADC 63. Microcontroller 61 also includes a PWM module 62. Audio amplifier 64 utilizes Vcc as a power input and both the amplifier and the voltage-input resistor 66 are grounded with chassis ground 27. FIG. 7 and speaker detection circuit 70 is yet another variation on this theme, with precision low resistance resistor 76 in series between power source Vcc and amplifier 74. The microprocessor 71 may be the same as other microprocessors mentioned above, or it may include a different software program attuned to the specific circuit of FIG. 7. PWM module 72 and ADC 73 may also be the same or may be different from the PWM modules in other examples discussed above. Speaker 75 receives power from amplifier 74, which is connected to chassis ground 77.

Figure 8:
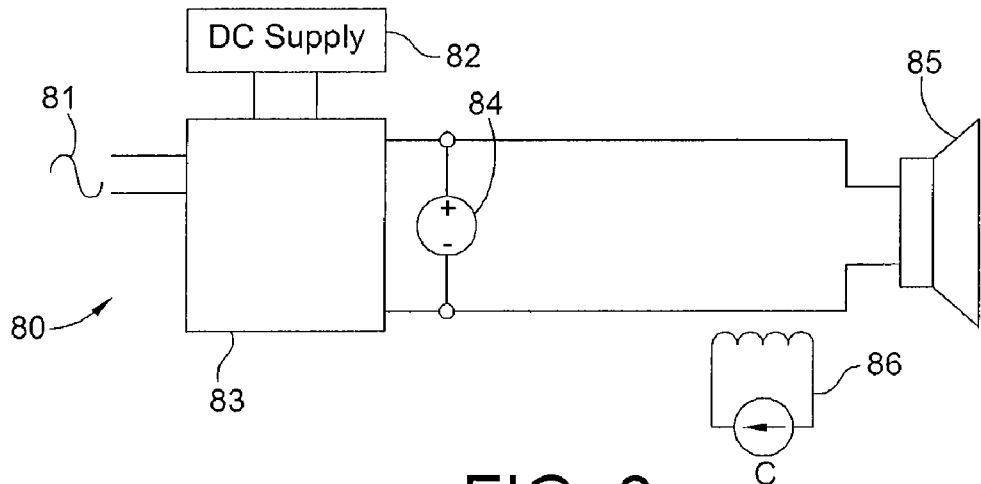
Figure 9:
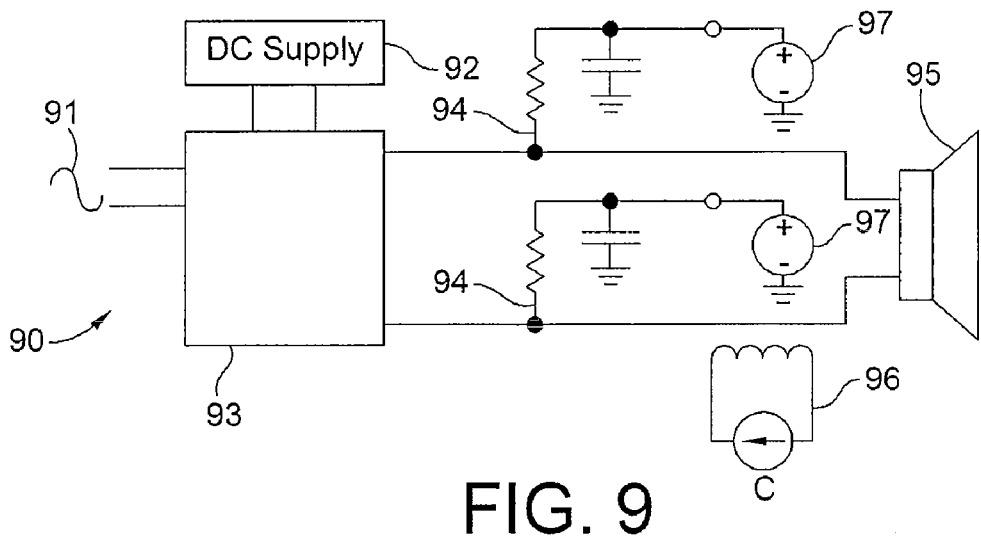

Yet another technique is disclosed in the circuit of FIG. 8. In detection circuit 80, an audio signal 81 is input into amplifier 83, with an amplifier power supply 82. Differential voltage probe 84 is connected between the leads to speaker 85 to detect the voltage to the speaker. Current transformer (CT) probe 86 is also used to detect the current flowing in the circuit. The voltage and current readings are then sent to an ADC or other signal processing circuitry, such as a digital signal processor (DSP), to determine a voltage, current, or power waveform for the speaker 85, in the same manner used in the previous methods described. The detection circuit 90 of FIG. 9 is similar. Audio signal 91 is input to power amplifier 93, which is powered by DC power supply 92. The voltage on each lead to speaker 95 is monitored by a grounded voltage probe 94. Each probe is equipped with a current limiting resistor and a small capacitor, e.g., 47 pf, in addition to a voltage sensor 97. Voltage sensor 97 may be a precision resistor or other voltage measuring device and may have a direct input to an ADC connected to the microprocessor or microcontroller. Current probe 96 detects the current in circuit 90 and sends a signal indicative of the current to a microprocessor or DSP for calculation of the waveform and a decision on whether the speaker is operational.

Figure 10:
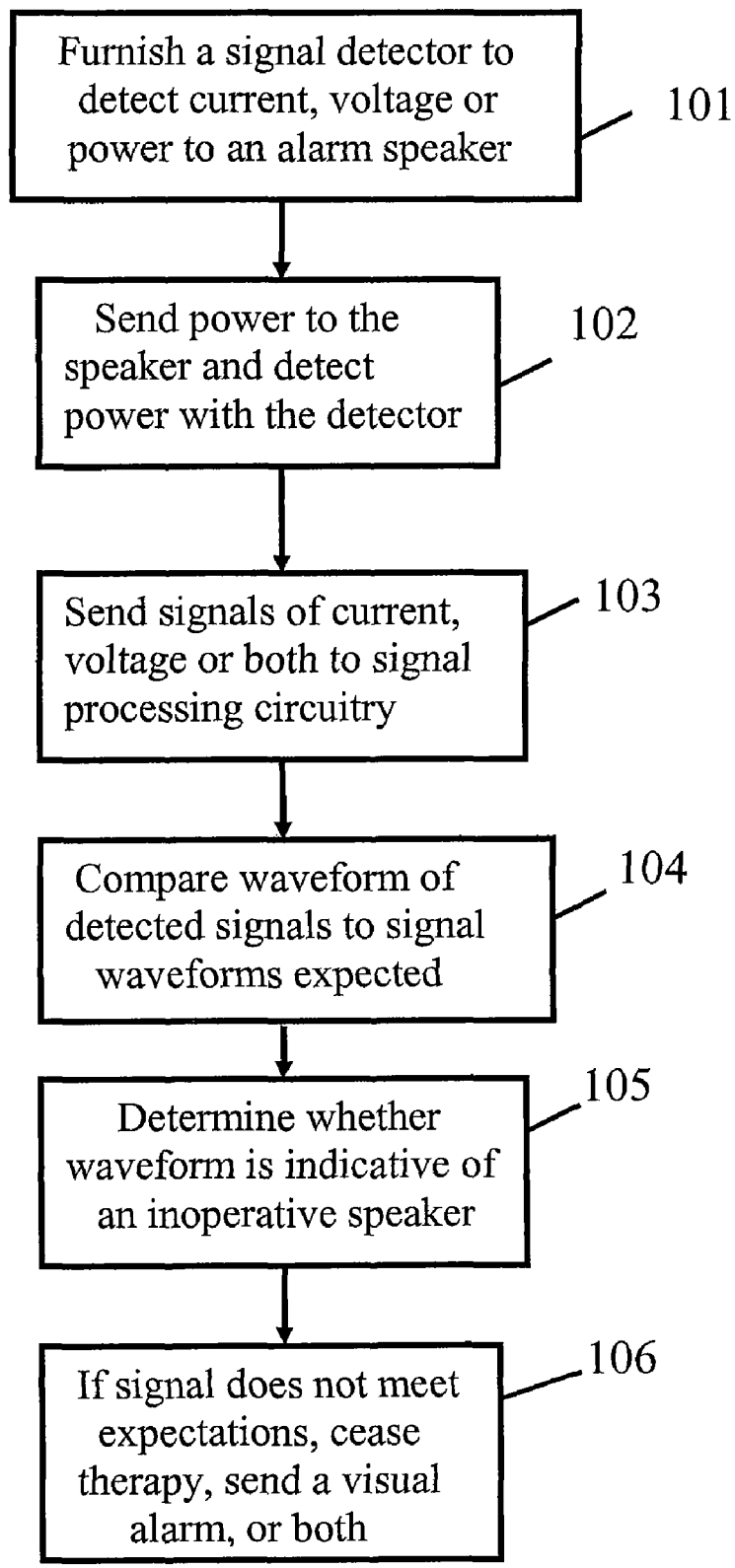
FIG. 10 is a flowchart depicting a method for operating a dialysis machine and verifying speaker operation.

The circuits described above can be used in a method of operating a dialysis machine, such as a peritoneal dialysis machine or a hemodialysis machine. The circuits described above may be incorporated as part of the dialysis machine. In other methods, the circuits described above, or other audio speaker operation detection circuits, may be made a part of an extracorporeal blood processing machine, such as a hemodialysis machine or an apheresis machine. One method of operating these machines is depicted in the flowchart of FIG. 10. The first step 101 of the method is to furnish a signal detector to detect, current, voltage or power to an alarm speaker. The signal detector does not necessarily require additional parts, in that the microprocessor may have sufficient memory for the required software, an analog-to-digital converter (ADC) may already be available in the machine control section, and so forth. Even the current-measuring or voltage-measuring resistor may already be available by using a spare resistor or trace already present in circuitry of the machine.

In operation, the control system then sends 102 power to the audio speaker to detect current, voltage, or power with the detector. The detector circuit then sends 103 signals indicative of speaker consumption of current, voltage, or power to signal processing circuitry. The signal processing circuitry converts the analog signals of a speaker to digital signals useful for comparison, and a computer program then compares 104 the detected signals to the signal waveforms previously detected in operation of speakers that are known to be operating properly. A look-up table of such expected signals and their characteristics or parameters may be stored in memory of the microcontroller or in a memory accessible to the microcontroller.

Using guidelines and logic from the program, the microcontroller and the computer program then determine 105 whether the waveform is indicative or characteristic of an operational speaker or whether the speaker appears inoperable. If the waveform conforms to the expected model, the sampling of data may be repeated periodically, as in a "test cycle" or start-up procedure. Alternatively, if the waveform conforms to expectations, no action need be taken. If the waveform appears to be consistent with damage or non-operation of the speaker, the microcontroller may cause 106 any therapy to cease, or may not allow therapy to begin if it fails a power-on self test (POST). The microcontroller may then send a visual alarm to alert operators or caregivers. The visual alarm may take the form of a alert message or sequence on a computer screen or by illuminating LEDs or flashing lights on a therapy machine. The machine may also be shut down or placed into a "safe" state if the waveform comparison or other check is not consistent with a correctly-functioning speaker.

In addition to the ways discussed above to discern an incorrectly-functioning speaker, there are many other ways. For example, rather than looking at ringing or oscillation in the waveform, spectrum analysis of the sensed waveform may be used. This could include FFT (Fast Fourier Transform) or other spectrum analysis. As with the other techniques used, a FFT transform or other spectrum of the resultant current waveform may be made and compared with a reference spectrum, or known good spectrum, to determine whether the speaker is functioning correctly.

Before any detection or sampling, the signal may first be filtered, such as by sending the signal through a high-pass filter. For example, if the fundamental frequency of the input voltage waveform is from about 100-200 Hz, a high pass filter that removes the fundamental components would allow easier detection of the ringing features of the resultant waveform. The high pass filter may be used for type A and B amplifiers. For type D, differential amplifiers, a low-pass filter for eliminating noise may yield better performance. In testing to date, the circuits described herein have worked for types A, B and D amplifiers.

Other ways of processing the signals may be used to detect power consumption by the speaker. It is understood that a square wave is a composite signal made of a fundamental sinusoid and the odd sinusoid harmonics. It is more convenient, in some cases, to think of a square wave as merely a simple square or trapezoidal signal in the time domain (rather than the frequency domain). By subtracting the input waveform from the output waveform, the result is a distinctive signal that is indicative of the speaker's mechanical and electrical characteristics. The resultant waveform may be easier to detect and process.

Other techniques may also be used in the detection circuit. For example, the waveform may be sensed as a current or a voltage by sensing the waveform across the terminals of the speaker, or by using a current-sensing resistor in series in the circuit. A non-contact sensor may be used, such as an inductively-coupled current transformer, or a hall-effect sensor, to detect the waveform. Alternatively, the resultant waveform may be sensed by capacitively coupling to the speaker wires or circuit board traces.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method for verifying operation of a speaker for a dialysis machine, comprising:
   generating an audio alarm for the dialysis machine by sending electric power to a speaker;
   sensing a waveform of the electric power;
   verifying the waveform conforms with a power consumption by the speaker; and
   visually alarming or placing the dialysis machine in a safe mode if the waveform fails to conform with a reference waveform of a correctly functioning speaker.

2. The method of claim 1, wherein the step of verifying comprises generating a second waveform and subtracting one of the waveform and the second waveform from the other of the waveform and the second waveform.

3. The method of claim 1, wherein the step of verifying the waveform comprises comparing an amplitude or a period of the waveform to a desired amplitude or desired period.

4. The method of claim 1, wherein the step of sensing the waveform is accomplished by sensing the waveform across a current-sensing resistor.

5. The method of claim 1, wherein visually alarming includes at least one of displaying an alert message or sequence on a display screen, illuminating a light emitter diode ("LED") on the machine, and flashing a light on the machine.

6. The method of claim 1, wherein the electrical power is sent to the speaker amplified by a single-ended power amplifier or a differential output power amplifier.

7. The method of claim 1, wherein the waveform is sampled for sensing by an analog to digital converter (ADC) capable of accepting a single-ended input or an ADC capable of accepting a differential input.

8. The method of claim 1, wherein the step of verifying that the waveform is consistent is accomplished by a computer or microprocessor software program.

9. The method of claim 1, wherein the sensed waveform is a current or a voltage.

10. The method of claim 1, wherein the step of verifying that the waveform is consistent is accomplished by comparing a current or a voltage downstream of the speaker with an expected current or voltage.

11. A method for verifying speaker operation, comprising:
    generating an audio alarm in a medical therapy machine by sending electric power to a speaker;
    sensing a waveform of the electric power;
    verifying the waveform conforms with a power consumption by the speaker of the medical therapy machine by comparing an amplitude or a period of the waveform to a desired amplitude or desired period; and
    visually alarming if the amplitude or period fails to conform with the desired amplitude or desired period.

12. The method of claim 11, wherein the waveform is sampled by an ADC and verified by a computer program that compares the sampled waveform with an expected waveform.

13. The method of claim 11, wherein the waveform is sensed by failure to sense a current or a voltage, indicating a failure or an open or shorted circuit.

14. The method of claim 11, wherein speaker operation is verified by noting a ringing on a current waveform.

15. The method of claim 11, wherein changed speaker operation is verified by noting a change in a current or voltage waveform of the electric power.

16. The method of claim 11, wherein the step of verifying is performed by comparing the sensed waveform to a known good waveform previously generated by the speaker.

17. A method for verifying speaker operation, comprising:
    generating an audio alarm by sending electric power to a speaker for a medical therapy machine;
    sensing a current or a voltage of the electric power;
    verifying with a computer program that the current or the voltage conforms with a power consumption by a known good speaker by comparing an amplitude portion or a period portion of the current or the voltage to a desired amplitude portion or desired period portion; and
    visually alarming if the current or voltage fails to conform with the power consumption by the speaker.

18. The method of claim 17, wherein visually alarming includes at least one of displaying an alert message or sequence on a display screen, illuminating a light emitter diode ("LED") on the machine, and flashing a light on the machine.

19. The method of claim 17, wherein the audio alarm is an access disconnect signal of a dialysis machine.

20. The method of claim 17, wherein the audio alarm is an operational alarm from a hemodialysis machine or a peritoneal dialysis machine.

21. The method of claim 17, wherein the audio alarm is an operational alarm from an extracorporeal blood treatment device.

22. The method of claim 17, wherein the step of verifying is accomplished by using a spectrum analysis or a FFT analysis of the current or voltage.

23. The method of claim 17, wherein the current or voltage is sensed in a non-contact manner, optionally using a current transformer or a hall-effect sensor.

24. The method of claim 17, further comprising filtering a signal generated by the current or the voltage before the step of verifying.

* * * * *